United States Patent [19]

Munnerlyn et al.

[11] 4,260,227

[45] Apr. 7, 1981

[54] AUTOMATED KINETIC PERIMETRY APPARATUS AND METHOD

[75] Inventors: Charles R. Munnerlyn, Sunnyvale; Lawrence R. Joba, Cupertino; Ramakrishna Shanker, Mountain View, all of Calif.

[73] Assignee: Coherent, Inc., Palo Alto, Calif.

[21] Appl. No.: 839,315

[22] Filed: Oct. 4, 1977

[51] Int. Cl.³ .............................. A61B 3/02; A61B 3/06
[52] U.S. Cl. ...................................................... 351/24
[58] Field of Search .................... 351/24, 39; 128/2 T

[56] References Cited

U.S. PATENT DOCUMENTS 3,414,348  12/1968  Gambs ................................... 351/24
3,705,003  12/1972  Lynn et al. ........................ 351/23 X

OTHER PUBLICATIONS

Jerome A. Gans, "Considerations . . . Tester, " *Med. Res. Eng.*, vol. 10, No. 6, Dec. 1971.

*Primary Examiner*—Paul A. Sacher
*Attorney, Agent, or Firm*—Limbach, Limbach & Sutton

[57] ABSTRACT

A Goldmann-type perimeter is provided which automatically performs kinetic perimetry without the need for manual intervention.

2 Claims, 8 Drawing Figures

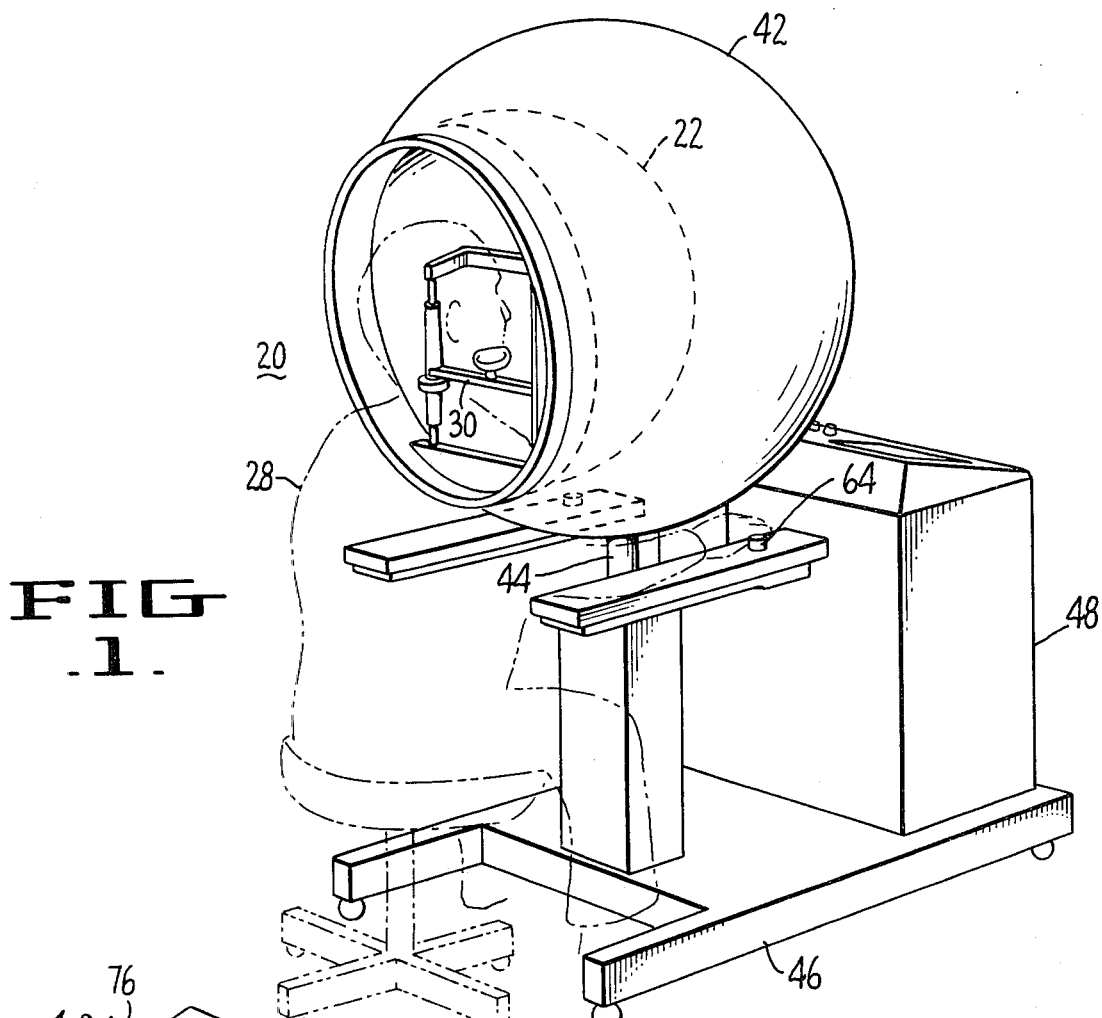
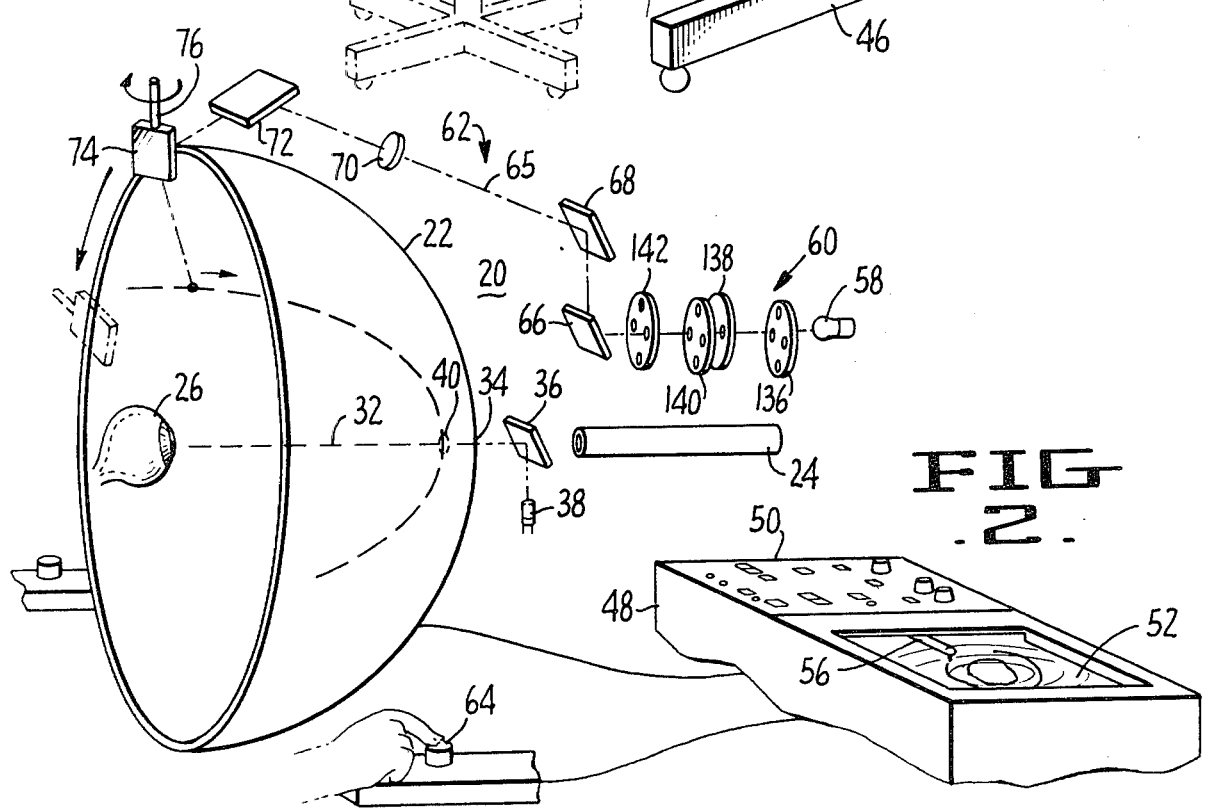

AUTOMATED KINETIC PERIMETRY APPARATUS AND METHOD

BACKGROUND OF THE INVENTION

The present invention relates to perimetry and more specifically to an automated method and apparatus of kinetic perimetry.

A visual field chart is a contour map of a patient's field of vision. Visual field examinations are designed to test differential light sensitivity of the eye of a patient. The difference threshold is the smallest measurable difference in luminance between a stimulus (target) and a field of comparison (background). The results of such examinations are typically plotted on a visual field chart.

Testing the field of vision of a patient is important to ophthalmologists, neurosurgeons and others interested in diseases affecting the brain and visual system. The pattern of deviation from normal visual fields can be used by a physician to localize the lesion to a certain part of the eye or brain, help the determine the activity and prognosis of the disease process causing the defect and even suggest the precise diagnosis in some instances. Major causes of organic blindness, i.e. glaucoma, cataract, diabetes, other vascular diseases, uveitis, retinal detachment, senile vascular degradation, all have characteristic patterns of defect in the visual field, often showing these defects early in the disease process.

The ability to follow the progression of a disease process is an important function of visual field testing. This requires that testing be accurate and consistent. When the visual threshold values of a patient are measured, and those results are compared with those of normal subjects or of the same patient at an earlier time, an accurate, standarized, reproducible method of measurement must be available. The physical characteristics of the stimulation must thus be known and measurable. Regular standardization of the physical characteristics provides a guarantee for the reproducibility of the stimulation and is a first essential of visual field examinations.

Generally, visual field testing falls within two broad categories, kinetic and static perimetry. In kinetic perimetry a target is moved from a point outside the field of vision of the patient into the field of view of the patient. The patient responds when the target is first detected. In the case of static perimetry, targets are fixed spots that do not move but the size and/or intensity is increased until the patient sees the target stimulus.

Within these two general categories of perimetry, there are many approaches to visual field testing. Perhaps, the simplest is the "confrontation" test. Here, the examiner asks the patient to look at him and then brings his hand in from the side noting when the patient first sees it in his peripheral vision. This is a very crude form of kinetic perimetry.

Another simple form of kinetic perimetry is the tangent screen. This is a black felt cloth that is used to test the central 30° field of vision. The cloth is generally hung on the wall one meter away from the patient. The examiner uses a black wand with white targets of different sizes on the end. The examiner monitors the patient's fixation as he moves the white target across the black screen. Small pins are stuck into the felt to outline isopters, a contour line within which a patient sees a target of given size and intensity. The visual field map is then transfered from the wall felt to a standard paper chart. This method is quite imprecise since there is no standardization of room light, target movement, target intensity, etc.

The best known of the kinetic perimeters is referred to as the Goldmann-type projection perimeter. This type perimeter is named after Dr. Hans Goldmann, a European ophthalmologist who did much of the original design and testing on the hemispherical bowl concept. Available Goldmann-type perimeters are manually operated. The operator selects the target (stimulus), size and intensity, moves the target within the bowl, monitors patient fixation and records responses on the chart. In some cases, automatic recording is provided which provides for automatic marking of the field of vision chart each time the patient presses the response button.

Since the movement of the target spot within the hemispherical bowl is manual, extensive training and practice under the guidance of a physician or experienced perimetrist is necessary for the operator to learn how to use the perimeter. This training may take up to a year to teach a technician the necessary skills. Manually operated Goldmann type perimeters also require full time involvement of the technician.

There are numerous types of static perimetry devices described in the literature and in the market. Some use hemispherical bowls as used in Goldmann-type perimeters. Others use flat, rectilinear screens. Still others use cathode ray screens for the projection of target spots. In some cases, the selection of the spot size and/or intensity, the location of the target spot size, and the recordation of when the target is seen by the patient is done automatically. In some cases, this is carried out by the use of a programmed computer. See, for example, U.S. Pat. Nos. 3,664,732, 3,718,386, 3,883,234, 3,705,003 and 3,172,404. However, the fixed location of the target sports in the case of static perimetry lends itself to the use of automatic control means such as a programmed digital computer.

Automatic kinetic perimetry has not heretofore been accomplished. The problem of being able to automatically direct the target scan so as to accurately and correctly determine the field of vision of a patient is an extremely difficult and complex task. The visual field of a patient who has an eye disease is often very irregular and contorted, thus making it extremely difficult to provide non-manual scanning to insure a correct visual field test.

SUMMARY OF THE INVENTION

In accordance with the present invention a method and apparatus for providing automatic kinetic perimetry is provided. By automatic it is meant that kinetic perimetry is carried out without the intervention of a human operator. In the embodiment described, the target beam movement is under control of a programmed general purpose digital computer.

More specifically, a light source is provided for projecting a target spot within a Goldmann-type perimeter bowl. Control means automatically moves the position of the target spot within the perimeter bowl to determine points defining the visual field of the patient. The control means comprises means for moving the target spot along a continuous and closed path generally outside the field of view of the patient. During portions of the scan the target spot is visible to the patient. The closed path comprises a plurality of semi-closed loops or paths with the termination of each semi-closed loop being the point when the target spot is first seen by the patient during the visible portion of the semi-closed loop. The termination point of one semi-closed loop constitutes the beginning point of the next semi-closed loop. As used herein, a loop may comprise a curved path, a rectilinear path, or any series of segmented straight or curved lines.

Each visible or scan poration of the semi-closed loop follows a predetermined distance and length according to a predetermined set of rules. In the event that a visible scan does not result in it being seen by the patient, the target point is retraced and a new directional scan takes place. Each new scan is a function of the history of the previous scan. The programmed general purpose digital computer provides a set of rules which determines the sequence of scans depending upon what occurred on the last previous scan.

In the case of an unsuccessful scan, as stated above, the scan point, although not visible, is returned along the unsuccessful scan path. Thus, although there are occasional excursions from each semi-closed loop or path, such excursions only take place when a scan is unsuccessful and when it is unsuccessful the scan point returns along its path. This ensures the integrity of each semi-closed loop or path and ensures that the series of semi-closed loops or paths is continuous and uninterrupted.

BRIEF DESCRIPTION OF THE DRAWINGS

FIG. 1 is a perspective view of the automated kinetic perimetry apparatus of the present invention;

FIG. 2 is a partial view of the automated kinetic perimetry apparatus of FIG. 1 including an exploded view of a part of the target spot projection apparatus;

DESCRIPTION OF THE PREFERRED EMBODIMENTS

Figure 3:
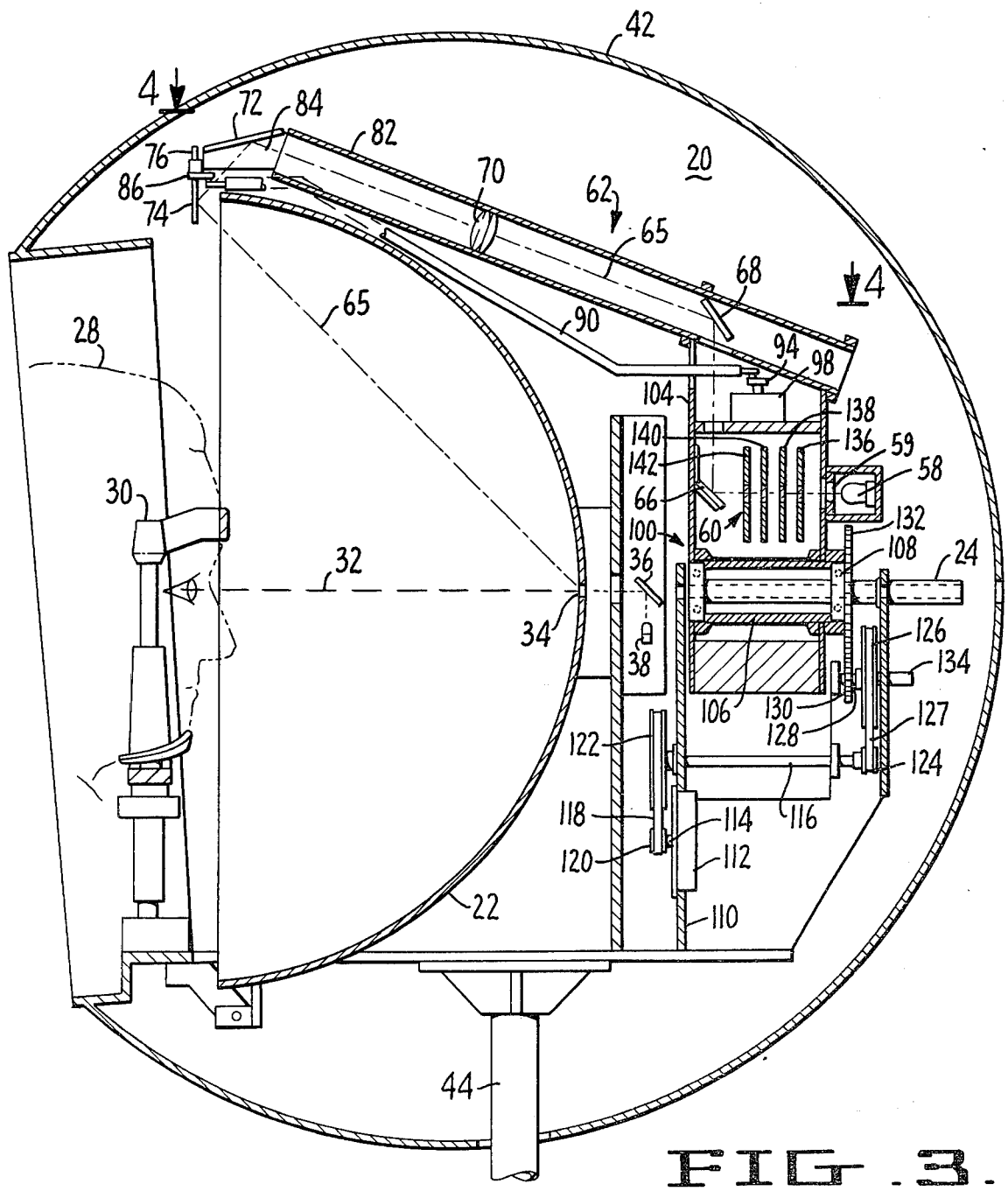
FIG. 3 is a cross-sectional view of the perimeter bowl of FIG. 1 and related apparatus.

FIGS. 1 and 2 show the automated kinetic perimetry apparatus 20 of the present invention. It includes a hemispherically-shaped Goldmann-type projection perimeter bowl 22 within which are projected target spots of light. The telescope 24 (FIG. 2) is provided so that the Examiner can observe the location or fixation of the eye 26 of patient 28. The head of patient 28 is positioned within a head rest assembly 30 with his eye 26 in line with the axis 32 of the perimeter bowl 22 and the axis of the telescope 24. Axis 32 passes through the center 34 of the bowl 22. As seen in FIG. 3, a hole is provided at the center point 34 for a line of sight.

It is important that the patient being tested looks at the center point 34 for proper testing. In part this is accomplished by means of the head rest 30. Additionally, the person giving the test can visually observe the eye through telescope 24 to insure that it is directed at the center point 34. Preferably, automatic sensing means is provided for automatically determining whether the axis of the eye 26 is properly aligned with axis 32. Various techniques are available for automatically monitoring the eye, as is known to those skilled in the art.

A beam splitter 36 is located at approximately 45-degree angle to the axis 32. Positioned at 90 degrees to the axis 32 and directed at beam splitter 36 is a suitable light source 38. The purpose of the light source 38 is to project a beam of light, preferably a colored light, such as red, as a spot 40 along the axis 32. This provides a reference point for the patient being tested in order to help maintain his eye properly fixed.

The perimetry bowl 22 is enclosed in a larger outer hemispherical bowl 42. The space between the two bowls 22 and 24 is taken up with the target spot projection assembly and the shutter assembly which will be described in more detail in connection with FIG. 4. The combination of the inner bowl 22, outer bowl 42 and head rest assembly 30 is supported by a column 44 which in turn is supported by support base 46.

Base support 46 also supports console 48. Console 48 houses a general purpose digital computer, which, when programmed, automatically performs the target spans required for kinetic perimetry. Located on the top of the console is a control panel 50 and a visual field chart holder 52. The chart holder 52, shown in greater detail in FIG. 5, holds a visual field chart 54 which is used to record and plot the response of the patient to the perimetry examination. A stylus 56 is used to mark points where the patient is able to see a target spot. The position of the spots which are first observed by the patient are stored within the computer in console 48. The computer can also be utilized to control stylus 56 to plot isopter lines between the observed points.

Light source 58 is provided to illuminate the inner perimeter bowl 22 and as a light source to project a beam of light to define a target spot on the interior surface of perimeter bowl 22. Light from the light source 58 is collimated by lens 59 and then passes through a shutter assembly 60 and through a target spot projection assembly 62 before being projected on the interior surface of hemisphere 22. As will be explained subsequently the shutter assembly regulates the size, intensity, color and rate of repetion of the target spot. The function of the target spot projection assembly 62 is to project the target spot within the perimeter bowl 22 and to move the target spot as required by the kinetic testing procedure of the subject invention.

During a kinetic perimetry examination the target spot is moved by the target projection assembly 62 from a point outside of the field of vision of the patient toward a point which is expected to be within the field of vision of the patient. When the patient first sees the target spot he pushes a response button 64 which is coupled to a programmed digital computer 180 (FIG. 8) within the console 48.

Figure 4:
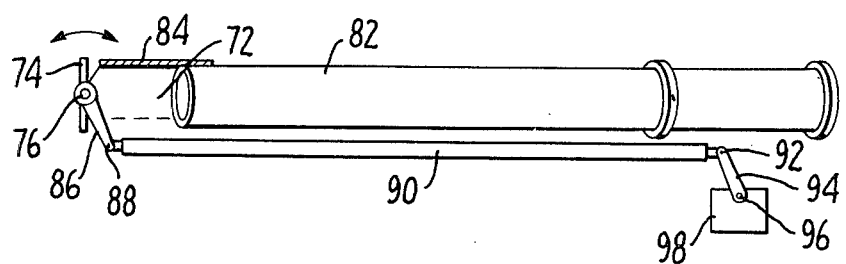
FIG. 4 is a top view of a part of the target spot projection apparatus of FIG. 3.

Details of the target spot projection assembly 62 can be seen by reference to FIGS. 2, 3 and 4. After passing through the shutter assembly 60 the light beam 65 from light source 58 is reflected by a pair of mirrors 66 and 68. Thereafter, the light beam 65 passes through focusing lens 70 and is reflected once again by mirror 72 onto object mirror 74. Mirror 74 has two directions of freedom. First, it is rotatable about axis 76. Second, the entire mirror is movable in a circular path which is generally concentric with the outer perimeter of the perimeter bowl 22.

Figure 6:
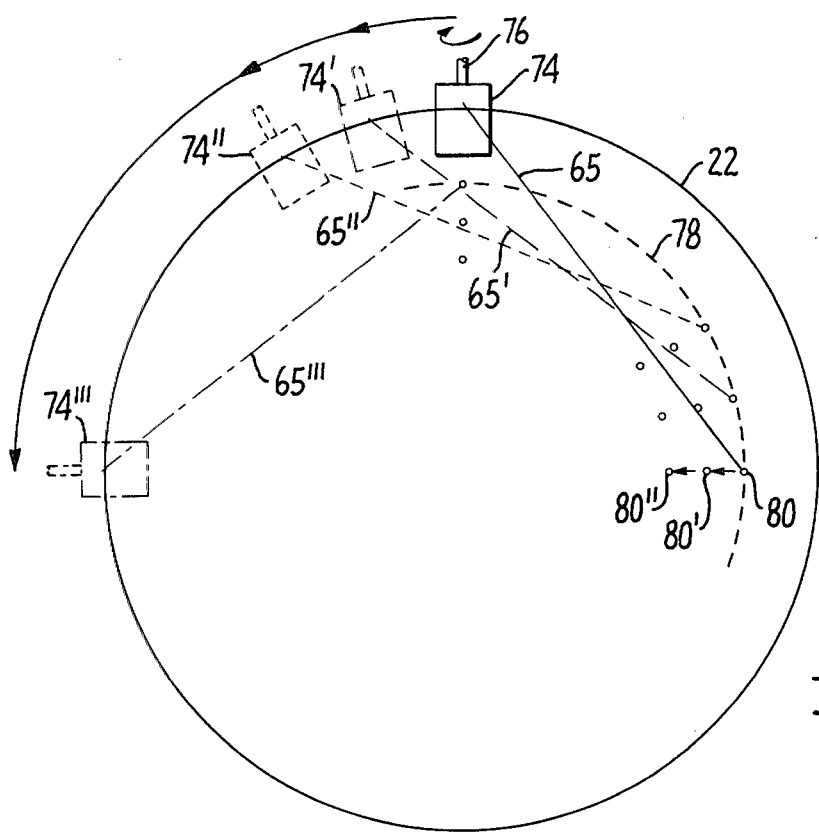
FIG. 6 is a view directed toward the interior of the perimeter bowl of FIG. 3.

The movement of the object mirror 74 and the resulting affect on the projection of beam 32 within the perimeter bowl 22 is best seen by reference to FIG. 6. Mirror 74 is shown in solid lines at the top of bowl 22 in FIG. 6 as it is shown in FIGS. 2 and 4.

The position indicated by 74' shows the object mirror 74 as it is rotated counterclockwise facing the interior of hemispherical bowl 74. Of course it can be rotated clockwise also, but this directional movement will illustrate its operation. It can be seen that the affect of moving the mirror 74 to the point at 74' is that the reflected beam moves along to a different position on the same radial or parallel 78. This is true in the case of the object mirror 74 being in the position of 74" and 74"', so long as the object mirror 74 is not rotated on its axis.

To move the target spot 80 along a meridian towards the center of the perimeter bowl 22 the object mirror 74 is rotated about its axis 76. This may be seen by the movement of the target spot to the position 80' and 80" as the mirror 74 is rotated in FIG. 6.

The mechanism for rotating the object mirror 74 about its axis 76 is shown in FIGS. 3 and 4. FIG. 3 shows a top view of a part of the target projection assembly 62. A light enclosure tube or arm 82 houses the focusing lens 70 and is also used to mount the reflecting mirror 72. Mirror 74 is rotatably mounted on an axle about its axis 76 by a suitable bearing support which in turn is supported by a flange 84 attached to arm 82 which also supports mirror 72. Extending from the axle 76 is a lever arm 86 which is pivotally attached at 88 to rod 90. In turn rod 90 is pivotally attached at 92 to arm 94 which is attached to the shaft 96 of a DC servomotor 98. In other words, arm 86, rod 90 and arm 94 form the linkage between the DC servomotor 98 and the object mirror 74.

The shaft from DC motor 98 is coupled to the arm 94 through a worm gear which permits the mirror 74 to be rotated over a 90-degree angle. Since the angle of a reflected light beam from a mirror is rotated two degrees for each degree of rotation of the mirror, this permits the target beam to be rotated over a 180-degree angle within the perimeter bowl 22. Also coupled to the worm gears from the DC servomotor 98 is a position potentiometer (not shown) which is used to sense the position of object mirror 74. This position signal is provided to the computer 180 in console 48.

Drive mechanism assembly 100 is used to rotate the object mirror 74 concentrically about the hemispheric bowl 22. Arm 82 is mounted to a drive housing 104 which is rotatably mounted on stationary shaft 106 via bearings 108. Shaft 106 also serves as the telescope 24 enclosure. The entire drive housing 104 is mounted by a support 110.

Drive housing 104, and hence the object mirror 74, is rotated by a DC servomotor 112 attached to the drive housing 110. Like servomotor 98, servomotor 112 is under the control of the central computer 180. The motor shaft 114 is used to drive a second shaft 116 through an intermediary pulley 118 and a pair of step down pulley wheels 120 and 122. Another set of pulley wheels 124 and 126 and pulley belt 127 coupled to shaft 116 slow down the rotational velocity of the motor 112 even further.

Pulley wheel 126 is coupled to a shaft 128 which is terminated with a gear wheel 130. Gear wheel 130 engages a larger gear wheel 132 which is coupled directly to the drive housing 104. A potentiometer 134 is used to sense the position of shaft 128 and hence the position of the object mirror 74. This information is used by the computer 180 within the console 48.

The shutter assembly 60 comprises four disks or wheels. Aperture wheel 136 has 16 holes, each of a different diameter. Depending upon which aperture is aligned with the light beam 65 from light source 58 the desired spot size can be provided. Shutter wheel 138 consists of 12 openings and 12 closings. The shutter wheel can be rotated at varying speeds to provide a flickering target spot. If a steady target spot is desired then the shutter wheel is positioned so that an aperture is maintained aligned with the light beam.

Disk 140 is provided with 16 red, green, blue and white colored filters of varying light intensity around its periphery. Disk 142 is provided with 16 different intensity level filters, each having the capability of filtering out a different percent of light passing through it. The filters on disk 142 in combination with those on disk 140 allow light target beams of four different colors over a wide range of intensities to be projected within the perimeter bowl 22.

Each of the disks 136, 138, 140 and 142 is powered by its own individual stepping motors (not shown). For convenience and to enable the servomotors to be positioned in the space available, the aperture disk 136 and the color disk 140 are mounted so that their outer periphery is located along the axis of the light beam 65, as shown in FIG. 2. Similarly, the shutter wheel 138 and the intensity filter wheel 142 are located on the other side of the path of the light beam 65.

Each of the wheels 136, 138, 140, and 142 are optically encoded. A four bit binary code in used. This enables the position of each wheel to be sensed and the information sent to the computer 180. Each of the stepping motors for controlling each of the disks 136, 138, 140 and 142 is controlled by operation of the programed computer 180 in console 48.

Figure 5:
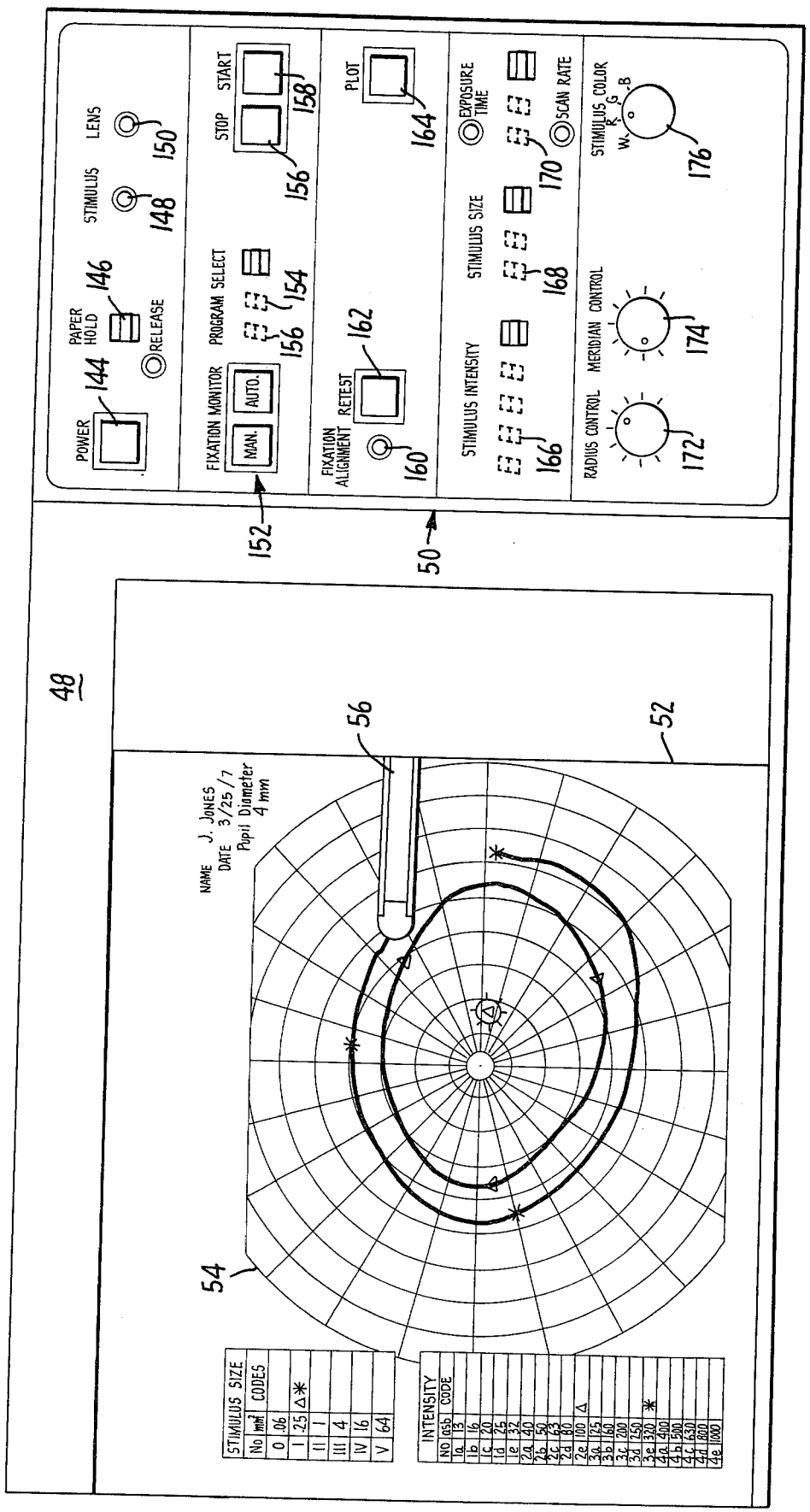
FIG. 5 is a top view of the control console of FIGS. 1 and 2.

Referring to the control panel 50 in FIG. 5 button 144 is the main power switch for turning on and off the perimetry apparatus 20. The paper hold button 146 activates an electrostatic hold down to maintain the visual field chart 54 within the field chart receptor 52. Stimulus light 148 is lit whenever the shutter 138 is on and a target spot is provided within the perimetry bowl 22. Lens light 150 when on indicates to the operator to put a corrective lens in or out of the view of the patient. Fixation monitor switches 152 are used to put the perimetry apparatus in a manual or automatic mode for eye fixation. In the normal mode, the automatic mode, the eye monitor detects loss of fixation and automatically tells the computer to retest.

The program select button 154 allows the operator to select the appropriate program. For example, although the perimetry apparatus of the present invention relates to kinetic perimetry, it can also be programmed to do static perimetry. The program selected is indicated by indicator lights 156. Stop button 156 is used to stop the test without losing data. Start button 158 is pressed to start tests and to lock in the automatic eye monitor. Fixation alignment button 160 goes on any time the patient's eye becomes misaligned. When in the manual mode, the operator starts the test over by pressing the retest button 162.

The plot button 164 is used at the completion of the text to plot out on a visual field chart 54 all the cumulative test points or to replot an entire test. The stimulus intensity display 166 provides a read-out of intensity in apostilbs; and allows the operator to select neutral density filters. The stimulus size display 168 displays the target spot, size and square millimeters, and allows the operator to select the stimulus size. The exposure time display 170 displays the kinetic speed, and allows the operator to select in degrees per second or fractions of a degree.

Where manual operation is desired manual radius control knob 172 and meridian control 174 is provided. The stimulus color knob 176 allows the operator to select white, red, blue or green target spots. As explained previously, the stimulus intensity, stimulus size, and stimulus color controls result in the appropriate selection of the positions on the disks 136, 138, 140 and 142.

Figure 7:
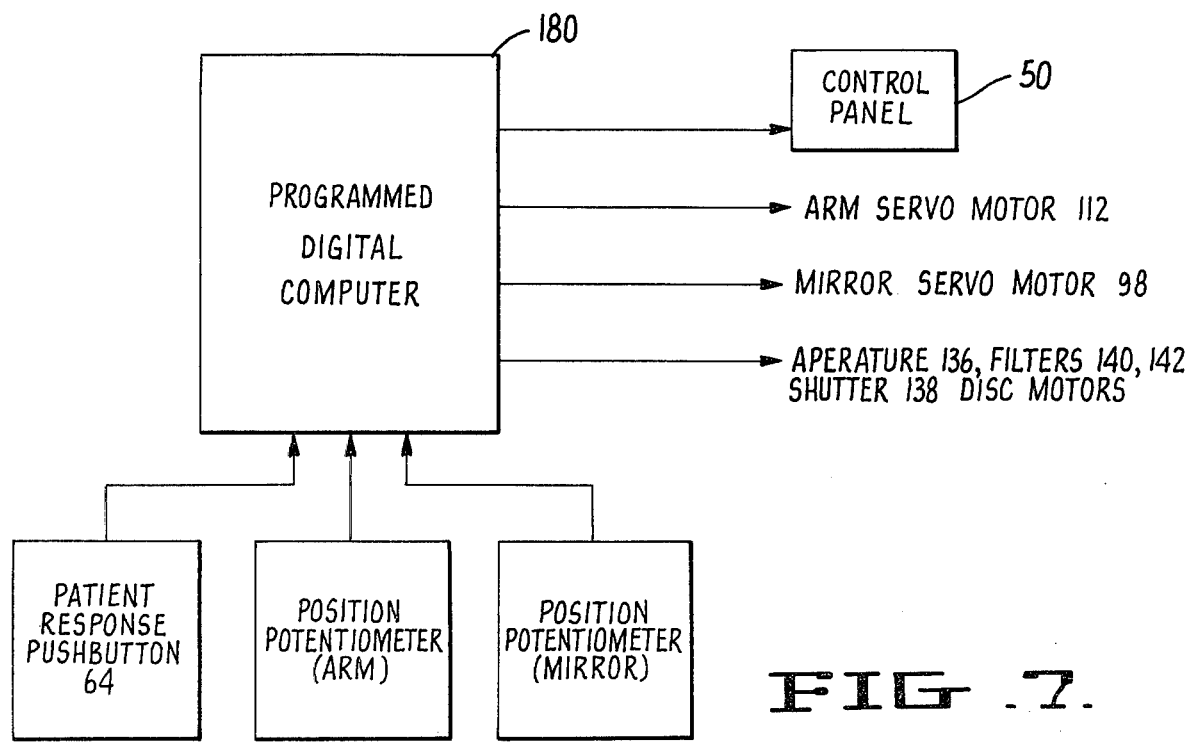
FIG. 7 is a generalized block schematic diagram of the major electronic components of the automated kinetic perimetry apparatus of the present invention.

FIG. 7 is a generalized block schematic of the major electronic components of the subject invention. The major control element is a programed digital computer 180. In one actual embodiment of the invention the computer used was an Intel 8080. The program for carrying out the subject invention is described subsequently.

Inputs to the programed digital computer 180 include the signals from the arm position potentiometer 134 and the mirror rotation position potentiometer (not shown). The programed digital computer 180 communicates in both directions with the control panel 50, as well as with the aperture 136 motor, shutter 138 motor, and color and intensity filters 140 and 142. The programed digital computer controls the arm servomotor 112 and the mirror servomotor 98 to control the position of the target spot on the inside of the perimetry bowl 22.

Figure 8:
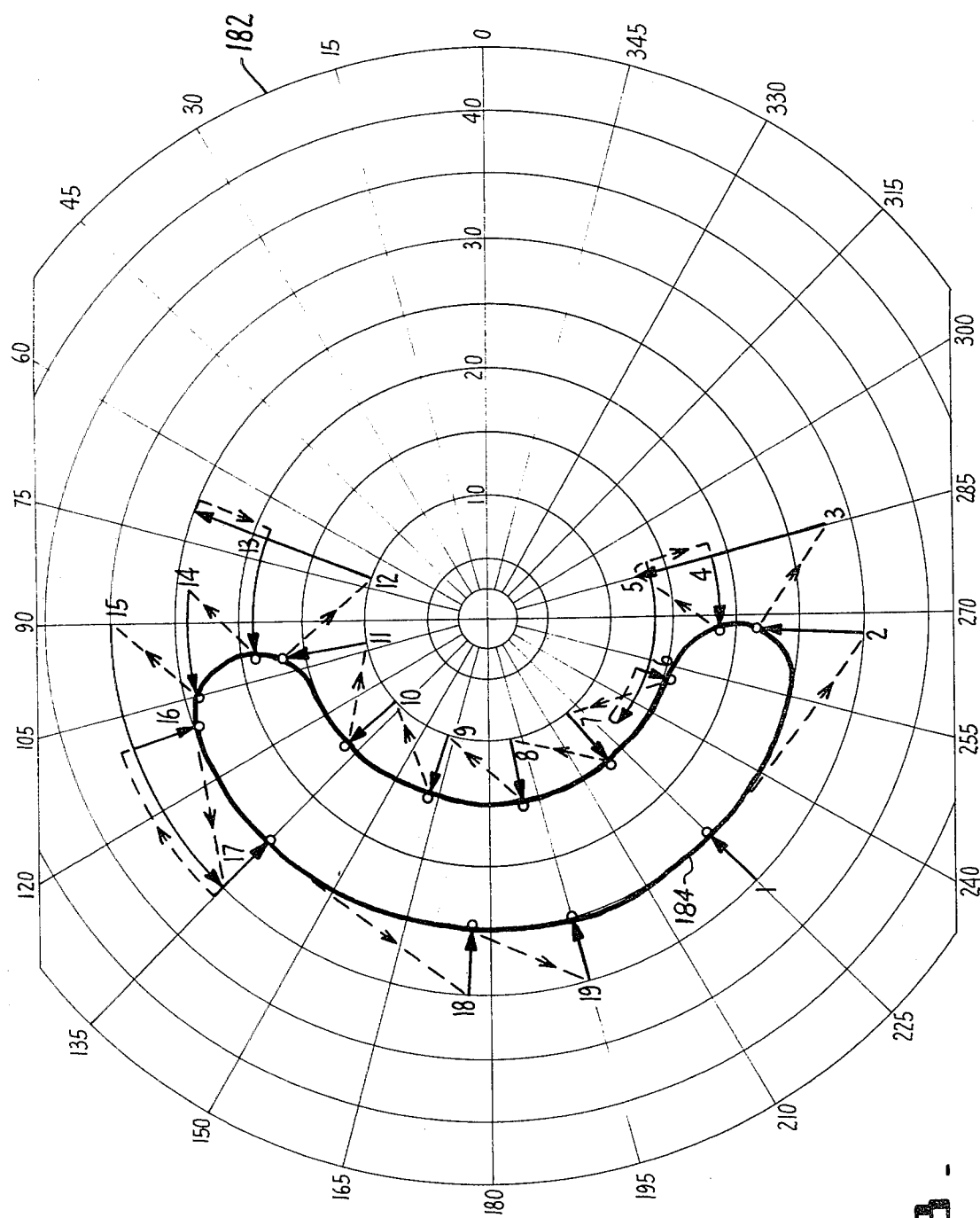
FIG. 8 is a field of view chart typically used in perimetry testing.

FIG. 8 is a field of view chart 182 used with Goldmann-type perimeter. While it covers only the central 45 degrees of the eye, other charts up to 90 degrees may be used. The visual field chart 182 is a circular configuration with polar coordinates marked thereon at 15-degree intervals by radially projecting lines called meridians. The chart also includes a plurality of concentric circles each called a radius or parallel which indicate the angle between axis fixation and a line to a particular point along one of the radially extending lines. The concentrically arranged radials or parallels are spaced five degrees apart in this particular chart. Using the two sets of coordinates any point on the surface of the kinetic perimeter 20 can be located. Isopters are drawn in kinetic perimetry to join points of equal visual sensitivity. Isopters are equivalent to contour lines on a topographic map.

In FIG. 8, isopter 184 represents the visual field of an eye of a patient who has poor vision in the central portion of the eye on the right-hand side of the eye. Located at points along the isopter 184 are a number of points represented by small circles. These points are generated by the perimetry apparatus of the subject invention in the manner to be described. By plotting these points the isopter 184 of FIG. 8 is created. The actual creation of the isopter 184 on the visual field chart of FIG. 8 is carried out through the direction of the programed computer 180. The area within the isopter 184 defines the area that the patient's eye has visibility for light stimulus of the intensity used during the test period.

A plurality of solid lines or scans indicated by the numbers 1–19 are shown outside of the field of vision of the patient as indicated by isopter 184. Each of these lines indicates the passing of the target beam spot across the surface of the perimeter bowl 22 during a test session. In those cases where the scan was perceived by the patient being tested, and he pushed the button 64 indicating that he had seen the light, the location of the target spot at that time is recorded by computer 180.

At the time that the patient perceived the scan, i.e. a "hit" took place, the target beam is turned off and is moved with the intention of having the target beam go outside of the field of vision of the patient, in a manner which is described subsequently. During the time that the apparatus is being repositioned for the next scan the target spot does not appear on the perimeter bowl 22. The dashed lines in FIG. 6 indicate the path of the target beam if the target spot were allowed to strike the surface of the perimeter bowl. As can be seen in FIG. 6 the path defined by the movement of the target spot, both while the target spot is "on" and while it is "off", defines a more or less enclosed path around the field of vision of the patient and, except for the points where the target beam is perceived by the patient, is outside of the field of vision of the patient.

It can be seen that in some cases a scan does not ultimately terminate by being perceived by the patient. As will be explained, this occurs if the particular scan never falls within the field of vision of the patient during the duration of the scan. In this case the direction of the scan is changed in accordance with a set of predetermined rules, which are described in more detail subsequently. In such cases where a scan fails to result in a "hit", the target spot is returned back along the direction it came before being redirected. It may be seen that the path of the target spot results in a series of interconnected semi-enclosed loops or paths with the termination of each semi-loop or path being the point at which the patient perceives a scan, and the same point constituting the beginning point of the next semi-enclosed loop or path.

The movement of the target spot is controlled by the programmed general purpose digital computer 180. The flow diagram for a computer program to carry out the automated kinetic scan technique of the present invention is shown and described in Appendix I. The computer listing (source code) for a computer program to carry out the requirements of the flow chart is set forth in Appendix III. Appendix II provides a definition of the program variables and a description of the instruction implementation used to interpret the computer program of Appendix III. Appendices I, II, and III, not printed herein, are included as part of the original file in the U.S. patent and Trademark Office.

In order to have a general understanding of the operation of the computer program to carry out the automated kinetic scan technique of the present invention, a description follows indicating how each of the 19 scans in the example of FIG. 8 are made. It should be understood that the following description is not intended to be complete or to explain every possible condition or action taken under the direction of the programmed computer. For a complete understanding of the computer program reference is made to the flow chart, Appendix I. It should be pointed out, however, that the following description should be useful not only to gain an understanding of the subject invention, but also as a guide to the use and interpretation of the flow chart (Appendix I), as well as the computer program itself (Appendix II and III).

For purposes of understanding the following description the following definitions are provided. These definitions do not necessarily represent the specific definitions provided in Appendix II; although, generally, they do agree with those definitions, but there are some differences.

+RAD. SCAN=Positive Radial Scan. this is a linear scan, going radially outwards, i.e. the starting radius is less than the ending radius.

−RAD. SCAN=Negative Radial Scan. This is a linear scan, going radially towards the center, i.e. the starting radius is less than the ending radius.

+ARC. SCAN=Positive Arc Scan. This is a counterclockwise arc scan about the center. When the left eye is being tested a +ARC. SCAN is a clockwise arc scan.

−ARC. SCAN=Negative Arc Scan. This is a clockwise arc scan about the center, counterclockwise for left eye.

RO=Radius−Origin. This is the starting radius of a scan.

TO=Theta−Origin. This is the starting meridian of a scan.

RT=Radius−Target. This is the radius of the end point of the scan.

TT=Theta−Target. This is the meridian of the end point of the scan.

Specifying RO, TO, RT, TT is enough to completely define the geometry of a scan. In the perimetry apparatus described herein the movement of the target spot is limited to only radial and circular arc scans. However, it is not intended that the subject invention should be limited to these particular scan limitations.

HIT=Patient Response. The patient responds by depressing push-button to indicate that he has seen the spot of light.

MISS=No Response. The patient failed to respond to a particular scan.

IMM. HIT=Immediate Response. The patient responded within a second of starting the scan. This implies that the scan started inside a region where he could see.

For the purpose of this example the following definitions of R and TH apply.

R=Radius of the point along the scan where the patient responded.

TH=Meridian of the point along the scan where the patient responded.

TS=Linear speed of the scan. In the particular apparatus described herein this is 3°/SEC up to a radius of 40°. 4°/SEC between 40° and 80° and 5°/SEC beyond 80°.

| SCAN NO. | |
|---|---|
| 1. | This is the first scan starting on the 225° meridian and going radially towards the center. |
| 2. | A HIT on a −RAD. SCAN is always succeeded by another −RAD. SCAN, usually, but not always, 30° away from the previous meridian. RO = R + 5<br>RT = R − 10 |
| 3. | This −RAD. SCAN did not get a HIT. So look under [−RAD., MISS = 1] in the "Grid Mode Reference Table" of the flow chart, Appendix I. |
| 4. | The (−RAD., MISS = 1) box from the "Grid Mode Reference Table" gives:<br>$\begin{bmatrix} TO = TO;\ TT = TO - 60° \\ RO = RT = RO - 10° \end{bmatrix}$ for Scan No. 4<br>which gets a HIT. Note this is a |

| SCAN NO. | -continued |
|---|---|
| 5. | −ARC. SCAN.<br>Since the last scan was −ARC and got a HIT, look under −ARC., MISS = 0 in the "Grid Mode Reference Table" which gives:<br>$\begin{bmatrix} RO = RT = RO - 5 \\ TO - TH + 20° \\ TT = TH - 40° \end{bmatrix}$ for Scan No. 5,<br>which is a miss. |
| 6. | Since the previous scan was a −ARC and a MISS, look under [−ARC., MISS − 1] which gives:<br>$\begin{bmatrix} RO = RO;\ RT = 25° \\ TO = TT = TO - 40° \end{bmatrix}$ (Maximum Radius of Isopter (S8))<br>This is a −RAD. SCAN and gets a HIT. |
| 7. | Since the last scan was a +RAD. SCAN and got a HIT, look under [+RAD., MISS = 0].<br>This gives:<br>$\begin{bmatrix} RO = R - 5 \\ RT = R + 10 \\ TO = TT = TH - 3° \end{bmatrix}$ |
| 8, 9, 10, 11 | are explained in the same manner as Scan No. 7 |
| 12. | The previous scan, Scan No. 11, was a +RAD. SCAN and got a hit, so this scan is a −RAD. SCAN just as in Scan No. 8. However, this scan gets a MISS. |
| 13. | The last scan was a +RAD. and was missed, so look under [+RAD., MISS = 1] in the "Grid Mode Reference Table".<br>This gives:<br>$\begin{bmatrix} RO = RT = RO = \left[\dfrac{RT - RO}{2}\right] \\ TO = TO \\ TT = TO + \dfrac{600}{RO} \end{bmatrix}$<br>This +ARC. SCAN gets a HIT. |
| 14. | Since the last scan was a +ARC. HIT, look under [+ARC., MISS = 0] in the "Grid Mode Reference Table", which gives:<br>RO = RT = RO + 7<br>TO = TH − 12°<br>TT = TH + 24°<br>This is another +ARC. SCAN that gets a HIT. |
| 15. | Since the last scan was a +ARC. HIT the same rule is used that gave Scan No. 14, however, this +ARC. SCAN gets a MISS. |
| 16. | Since the last scan was a +ARC. MISS look under [+ARC., MISS = 1] in the "Grid Mode Reference Table" which gives:<br>$\begin{bmatrix} RO = RO \\ RT = RO - 15° \\ TO = TT = TO + \dfrac{600}{RO} \end{bmatrix}$ for −RAD. SCAN and gets a HIT. |
| 17. | Since the last scan was a −RAD. HIT the same procedure is used as in Scan No. 2 to do −RAD. SCANs at 30° intervals. This scan gets a HIT. |
| 18., 19. | Same as Scan No. 17 and the next scan (No. 20) would be the same as Scan No. 1, so the program stops after Scan No. 19. In other words, the scan is not actually repeated to complete the path around the isopter since it is not needed. |

We claim:
1. Apparatus for kinetic perimetry comprising:

a bowl perimeter having an axis through its centerpoint;

means for locating the head of a patient being tested so that the axis of the patient's eye is approximately aligned with the axis of said bowl perimeter;

light source for projecting a target spot to a desired point of projection within said bowl perimeter;

control means for automatically moving the position of the target spot projection point relative to said bowl perimeter and for selectively projecting the target spot onto said bowl perimeter to determine points defining the visual field of the patient; and said control means comprising means for moving the point of projection of the target spot along a continuous and closed path generally outside the field of view of the patient, said closed path comprising a plurality of semi-closed loops, during a portion of which the target spot is projected onto and scans said bowl perimeter and is visible to the patient, with the termination of each semi-closed loop being the point when the visible target spot is first seen by the patient during the semi-closed loop, and with the termination point being the beginning point of the next semi-closed loop.

2. Apparatus for kinetic perimetry comprising:

a hemispherically shaped perimeter bowl;

apparatus for positioning the eye of a patient in line with the axis of said perimeter bowl;

means for automatically scanning a target light spot within said perimeter bowl from a plurality of positions and directions outside of the field of vision of the eye of the patient, to points on said perimeter bowl where the target light spot is first seen by the patient; and wherein said automatic scanning means includes means for moving each new scan from a position and in a direction dependent upon the result of the previous scan.

* * * * *

UNITED STATES PATENT AND TRADEMARK OFFICE
CERTIFICATE OF CORRECTION

PATENT NO. : 4,260,227
DATED : April 7, 1981
INVENTOR(S) : MUNNERLYN ET AL.

It is certified that error appears in the above-identified patent and that said Letters Patent are hereby corrected as shown below:

Column 2, line 38, delete "sports" and add --spots--.

Signed and Sealed this

Twenty-fourth Day of November 1981

[SEAL]

Attest:

GERALD J. MOSSINGHOFF

Attesting Officer     Commissioner of Patents and Trademarks